United States Patent
Hayoz

(10) Patent No.: US 10,058,427 B2
(45) Date of Patent: Aug. 28, 2018

(54) ADJUSTABLE ANNULOPLASTY RING AND SYSTEM

(71) Applicant: KEPHALIOS S.A.S., Paris (FR)

(72) Inventor: Daniel Hayoz, Villars sur Glâne (CH)

(73) Assignee: Kephalios S.A.S., Paris (FR)

( * ) Notice: Subject to any disclaimer, the term of this patent is extended or adjusted under 35 U.S.C. 154(b) by 0 days.

(21) Appl. No.: 15/031,321

(22) PCT Filed: Oct. 25, 2013

(86) PCT No.: PCT/EP2013/072378
§ 371 (c)(1),
(2) Date: Apr. 22, 2016

(87) PCT Pub. No.: WO2015/058808
PCT Pub. Date: Apr. 30, 2015

(65) Prior Publication Data
US 2016/0256274 A1    Sep. 8, 2016

(51) Int. Cl.
*A61F 2/24*  (2006.01)
*A61F 2/48*  (2006.01)

(52) U.S. Cl.
CPC .......... *A61F 2/2448* (2013.01); *A61F 2/2445* (2013.01); *A61F 2002/485* (2013.01);
(Continued)

(58) Field of Classification Search
CPC ........ A61F 2/24; A61F 2/2448; A61F 2/2445; A61F 2/2451
(Continued)

(56) References Cited

U.S. PATENT DOCUMENTS

| 4,917,698 A | 4/1990 | Carpentier et al. |
| 7,588,582 B2 * | 9/2009 | Starksen ............. A61B 17/064 606/139 |

(Continued)

FOREIGN PATENT DOCUMENTS

| WO | 00/44311 A2 | 8/2000 |
| WO | 2006/097931 A2 | 9/2006 |

(Continued)

OTHER PUBLICATIONS

Russian Office Action issued in corresponding Russian Patent Application [to Follow].
(Continued)

*Primary Examiner* — Suzette J Gherbi
(74) *Attorney, Agent, or Firm* — Davis & Bujold PLLC; Michael J. Bujold

(57) ABSTRACT

An adjustable annuloplasty ring assembly (10) comprises a support ring (30), an adjustable ring (32) nested at least partly within the support ring, and at least one deployable pressing element (34) for deforming the adjustable ring using the support ring (30) as support. Plural pressing elements (34) may be used at different positions around rings. Each pressing element (34) may have a variable extents of deployment, to vary the extent of deformation of the adjustable ring at the position of the pressing element. Each pressing element may comprise a deflectable blade (40), and the state of the blade may be retained by a ratchet (50). The pressing elements may be operated in a predetermined controlled sequence.

40 Claims, 4 Drawing Sheets

(52) U.S. Cl.
CPC . *A61F 2002/487* (2013.01); *A61F 2210/0004* (2013.01); *A61F 2250/001* (2013.01); *A61F 2250/0003* (2013.01)

(58) Field of Classification Search
USPC .................................................. 623/2.38–2.4
See application file for complete search history.

(56) References Cited

U.S. PATENT DOCUMENTS

| | | | |
|---|---|---|---|
| 9,078,747 B2* | 7/2015 | Conklin | A61F 2/24 |
| 2003/0220685 A1* | 11/2003 | Hlavka | A61F 2/2445 |
| | | | 623/2.11 |
| 2004/0122514 A1 | 6/2004 | Fogarty et al. | |
| 2004/0153146 A1* | 8/2004 | Lashinski | A61F 2/2451 |
| | | | 623/2.36 |
| 2005/0060030 A1* | 3/2005 | Lashinski | A61B 5/6882 |
| | | | 623/2.37 |
| 2005/0096666 A1 | 5/2005 | Gordon et al. | |
| 2006/0116757 A1* | 6/2006 | Lashinski | A61F 2/2451 |
| | | | 623/2.11 |
| 2007/0016287 A1 | 1/2007 | Cartledge et al. | |
| 2010/0076548 A1* | 3/2010 | Konno | A61F 2/2412 |
| | | | 623/2.1 |
| 2010/0076549 A1* | 3/2010 | Keidar | A61F 2/2445 |
| | | | 623/2.36 |
| 2011/0060407 A1* | 3/2011 | Ketai | A61B 17/00234 |
| | | | 623/2.37 |
| 2012/0221101 A1* | 8/2012 | Moaddeb | A61F 2/2445 |
| | | | 623/2.37 |
| 2012/0296419 A1* | 11/2012 | Richardson | A61F 2/2445 |
| | | | 623/2.36 |
| 2013/0006352 A1 | 1/2013 | Yaron | |
| 2013/0073031 A1* | 3/2013 | Brown | A61F 2/2466 |
| | | | 623/2.11 |
| 2014/0142695 A1* | 5/2014 | Gross | A61B 17/072 |
| | | | 623/2.37 |
| 2014/0163652 A1* | 6/2014 | Witzel | A61B 18/1492 |
| | | | 607/100 |
| 2014/0243963 A1* | 8/2014 | Sheps | A61F 2/2466 |
| | | | 623/2.11 |
| 2014/0336756 A1* | 11/2014 | Lee | A61F 2/2445 |
| | | | 623/2.37 |
| 2014/0350664 A1* | 11/2014 | Tozzi | A61B 17/12013 |
| | | | 623/2.11 |
| 2016/0045312 A1* | 2/2016 | Braido | A61B 5/6862 |
| | | | 623/2.37 |
| 2016/0135953 A1* | 5/2016 | Alon | A61F 2/2466 |
| | | | 623/2.11 |
| 2016/0310275 A1* | 10/2016 | Jin | A61F 2/2448 |
| 2017/0000609 A1* | 1/2017 | Gross | A61F 2/2445 |
| 2017/0027689 A1* | 2/2017 | Marcelli | A61B 5/6869 |
| 2017/0231507 A1* | 8/2017 | Manstrom | A61B 5/02007 |
| | | | 600/481 |
| 2017/0258585 A1* | 9/2017 | Marquez | A61F 2/2409 |
| 2017/0281337 A1* | 10/2017 | Campbell | A61F 2/2409 |
| 2017/0296340 A1* | 10/2017 | Gross | A61B 17/072 |

FOREIGN PATENT DOCUMENTS

| | | |
|---|---|---|
| WO | 2007/033360 A2 | 3/2007 |
| WO | 2009126629 A1 | 10/2009 |
| WO | 2012/084714 A2 | 6/2012 |

OTHER PUBLICATIONS

International Search Report Corresponding to PCT/EP2013/072378 dated Sep. 8, 2014.
Written Opinion Corresponding to PCT/EP2013/072378 dated Sep. 8, 2014.

\* cited by examiner

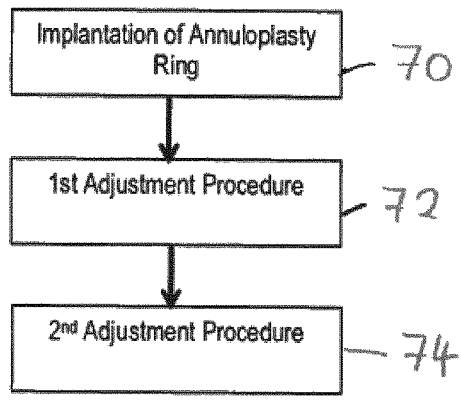
FIG. 4
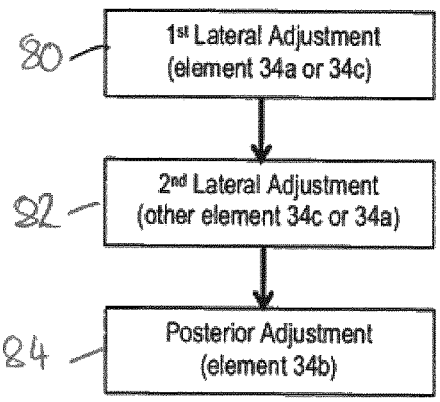 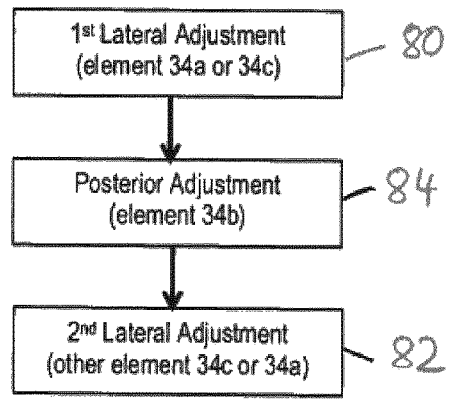
FIG. 5a   FIG. 5b

ADJUSTABLE ANNULOPLASTY RING AND SYSTEM

TECHNICAL FIELD

The present invention relates to an annuloplasty ring and system for repairing dysfunctional cardiac valves. In some non-limiting examples, the invention relates to an adjustable annuloplasty ring and system (for example, that can be adjusted within the body of a patient). Some non-limiting examples focus on treating atrioventricular cardiac valves such as the mitral valve or the tricuspid valve, but the concept, function and benefit are not limited to these valves.

BACKGROUND TO THE INVENTION

Annuloplasty (e.g. mitral or tricuspid annuloplasty) is the implantation of an annuloplasty ring (e.g., mitral ring or tricuspid ring) to deform and/or reinforce the valve annulus to correct incompetent valve function. During a classical annuloplasty procedure, the surgeon sizes the valve annulus and chooses a fixed size annuloplasty ring accordingly. This procedure is performed on the arrested heart under cardio-pulmonary bypass. However, the effectiveness of a fixed-size annuloplasty ring cannot be assessed during the procedure, because the heart is arrested. Only upon restarting the heart is it possible to assess whether the ring has had the desired effect to correct valve function. If the repair has not been successful, the patient has to undergo a second operation. Without the second operation, there remain certain possible long term consequences of a certain level of residual regurgitation. A further limitation of the classical procedure is that, after implantation of an annuloplasty ring, the size and geometry of the heart and the treated valve annulus may vary over time. Also for example, a dilated heart may respond to corrected valve function by returning to normal size. A fixed-size annuloplasty ring may, over time, become ineffective or inappropriate for the size of the valve annulus. causing recurrent mitral regurgitation and poor clinical outcome. The common practice is to implant too small rings in order to overcome the risk of residual regurgitation. Too small rings result in other problems such as too little blood flow through the mitral valve called mitral stenosis.

Adjustable annuloplasty rings that may be adjusted after implantation in the body have been proposed. By way of example, WO 2012/084714 proposes a partly adjustable annuloplasty ring system able to achieve limited control of an effective shape of the ring. The annuloplasty ring is an assembly comprising an external support ring, an inner adjustable ring, a permanent pressing element mounted between the external and inner rings, and actuating means designed to slide the pressing element around a circumference between the inner and outer rings. The assembly is adjustable by controlling the actuator means to move the pressing element to a desired position around the circumference, in such a way that a specific part of the inner ring at that position is deformed inwardly. An advantage of the assembly using external and inner rings is said to be that the adjustment can be performed without reducing a perimeter length of the inner ring, thereby reducing risk of valve stenosis.

In addition to above issues, a yet further complication that may occur following mitral valve repair and implantation of a mitral ring, is the problem of systolic anterior motion (SAM) in which the anterior mitral valve leaflet deflects towards the septum. SAM can be a cause of potentially life-threatening left ventricular outflow tract obstruction (LVOTO). There are several theories about possible causes of SAM, including possible influence of mitral valve rings on the mitral valve anatomy. When medical treatment is unable to correct it, re-intervention is necessary to correct SAM.

SUMMARY OF THE INVENTION

Non-limiting aspects of the invention may seek to enhance the versatility and custom adjustability of an annuloplasty ring and/or seek to mitigate one or more of the above issues.

Aspects of the invention are defined in the claims.

Additionally or alternatively, in one independent aspect of the invention, an adjustable annuloplasty ring assembly comprises a support ring, an adjustable ring nested at least partly within the support ring, and at least one pressing element deployable to deform the adjustable ring by using the support ring as a support, for adjusting the shape of the adjustable ring.

As used herein, the term "ring" (including "ring" assembly) is intended to cover any shape for circumscribing at least a majority of a periphery of a valve annulus. A ring may be closed (e.g., generally "O" shaped or generally "D" shaped) or a ring may be open (e.g., generally "C" shaped). A ring may be generally round or of generally circular geometry (e.g., generally "O" shaped or generally round-"C" shaped), or a ring may be non-round (e.g., generally "D" shaped or generally elongate-"C" shaped). A ring may be substantially symmetrical or substantially non-symmetrical in shape. A ring may optionally be split and/or may optionally extend around more than 360 degrees in some cases. A ring may be in a non planar 3D shape, e.g. generally a saddle-shape. The ring may generally have a three dimensional bent O-, C- or D-shape.

The adjustment of the annuloplasty ring can take place either peri-operative or post-operative. In the peri-operative mode, the adjustment is rather a "trial and error" approach. The aim is to fine tune the surgical results and eliminate either residual regurgitation or over-correction. In the post-operative mode, the valve area can be reduced in order to correct regurgitation and/or operating a more gradual size adjustment over time. Therewith, a long term treatment of the valve can be provided.

The at least one pressing element may optionally be carried by the support ring, or by the adjustable ring. In some embodiments, the at least one pressing element is carried by the support ring. The support ring may provide more accommodation room for the pressing element.

The ring assembly may further comprise one or any combination of the following features, which are all optional:

(A) In some embodiments, a plurality of deployable pressing elements may be provided at different positions around an interface between the support ring and the adjustable ring. Each pressing element may be deployable to deform the adjustable ring inwardly with respect to the support ring at the respective position of the pressing element.

Providing plural pressing elements can enhance the versatility of the annuloplasty ring assembly, and the ability to custom shape the adjustable ring for enhancing the efficacy of the annuloplasty ring assembly.

Each pressing element may be independently and/or individually deployable, for example, under control of a respective control member.

Preferably, the annuloplasty ring assembly comprises three pressing elements at predefined positions, preferably at the anatomical positions P1, P2, and P3, with respect to the mitral valve. With the two pressing elements at the P1, and P3 positions, the lateral distance of the valve may be adjusted, with the pressing element at the P2 position, the anterior-posterior distance may be adjusted.

(B) Additionally or alternatively, at least a portion of the (at least one) deployable pressing element may remain, in use during deployment of that pressing element, generally at a predetermined position along an (e.g., inner) periphery of at least one ring, for example, the support ring.

For example, the portion remaining at a predetermined position may be an end portion of a deflectable leaf member.

The portion remaining at a predetermined position may be generally immobile at least with respect to displacement along the periphery of the respective ring. Additionally or alternatively, the portion remaining at a predetermined position may pivot relative to the respective ring without displacement along the periphery of the ring.

Where plural deployable pressing elements are provided, in some embodiments, at least one of the pressing elements, and optionally all of the pressing elements, may have a respective portion that remains, in use, generally at a respective predetermined position around the (e.g., inner) periphery of the (e.g., support) ring.

(C) Additionally or alternatively, the (at least one) pressing element may be controllable to have a variable extent of deployment at the position of the pressing element, to define a variable deformation of the adjustable ring with respect to the support ring.

For example, a greater extent or state of deployment of the pressing element may cause greater inward deformation of the adjustable ring at the position of the pressing element.

The degree of deployment of the pressing element may be controlled by, for example, a control member coupled to the pressing element.

Providing a variable extent of deployment can enhance the versatility of the annuloplasty ring assembly, and the ability to custom shape the adjustable ring for enhancing the efficacy of the annuloplasty ring assembly. It can also enable the extent of deformation to be changed, for example, incrementally or progressively, following implantation.

The assembly may be configured for retaining a state of deployment of the pressing element after adjustment. For example, the assembly may comprise a latching (e.g. self-latching) mechanism for retaining the deployment state. The latching mechanism may comprise a ratchet. The ratchet may be configured (i) to obstruct relaxing of the pressing element from the deployment state, and (ii) to permit further (e.g., incremental or progressive) deployment of the pressing element to increase the deformation (e.g., at which the state of deployment may further be retained). In some embodiments, the latch (e.g., ratchet) may be controllably releasable so as to permit relaxing of the deployable pressing element.

Additionally or alternatively, the pressing element may be controllable between a plurality of predetermined different deployment states representing different extents of deployment, at each of which the deployment state is retainable. In some embodiments, the plurality of predetermined different states may correspond to retaining positions defined by a ratchet.

Where plural deployable pressing elements are provided, in some embodiments, at least one of the deployable pressing elements, and optionally all of the deployable pressing elements, may be provided with the variable deployment extent. Additionally or alternatively, the pressing elements may be relaxable, i.e. to reverse the deployment state at least to some degree. The different states may of predetermined different deployment states.

(D) Additionally or alternatively, the (at least one) deployable pressing element may comprise a deflectable blade configured to bow in response to application of mechanical force to at least one (e.g., end) of the blade.

In some embodiments. The blade may be carried by the support ring and configured to bow inwardly towards the adjustable ring in response to application of the mechanical force to the at least one portion (e.g., end) of the blade.

In some embodiments, the blade may have a shape, in a non-deployed position, that promotes bowing in a predetermined deployment direction (e.g., towards the adjustable ring) when the mechanical force is applied For example, the blade may have a non-straight shape, such as slightly bowed or convex (e.g., in a direction towards the adjustable ring).

Where plural deployable pressing elements are provided, in some embodiments, at least one of the deployable pressing elements, and optionally all of the deployable pressing elements, may comprise a respective blade.

(E) Additionally or alternatively, the (at least one) deployable pressing element may comprise fluid-deployable device.

The fluid-deployable device may, for example, comprise an inflatable bladder or balloon; and/or a movable diaphragm; and/or a piston within a cylinder.

The fluid may, for example, be a gas (e.g., for pneumatic control), or a liquid or gel (e.g., for hydraulic control).

In one form, a hardenable fluid e.g. cement may be introducible. The extent of deployment of the fluid-deployable device may remain adjustable while the inflation fluid remains fluid. The deployment state may become set when the fluid hardens. By hardening the fluid, any risks of accidental or natural leakage of fluid may be avoided.

In one form, a reversebly hardenable fluid is introduced. The fluid may be introduced in a liquid form at room temperature and polymerizes (jellifies) into a gel once warmed at body temperature. The fluid might be liquidized again by introducing e.g. cold liquid such as cold saline into the interface. The hardening of the fluid may also arouse as a result of physical means, i.e. light or chemical means, i.e. (catalyzers).

In one form, a non-hardenable fluid may first be introduced and retained during a period while further adjustment of the annuloplasty ring may be desired. Upon reaching a treatment stage such that no further adjustment is desired, the non-hardenable fluid may be replaced by (or augmented by) a hardenable fluid (or component), to set the final deployment state. the balloon or bladder may be adjusted peripoeratively in order to find the right size. The balloon or bladder is reversibly inflatable. After the right size has been found, the treatment stage is finalized and no further adjustments are desired, the bladder or balloon is deflated and removed. A stent may then be introduced to replace the bladder or balloon. A guide wire may be connected to the stent in order to further expand the stent if further adjustments are needed after some time.

(F) Additionally or alternatively, the (at least one) deployable pressing element may comprise one or multiple expandable stent.

The stent(s) may be expandable by an inflatable balloon or balloons. In some embodiments three stents may be arranged on a single cylinder balloon or multiple balloons or a shaped balloon. The stent(s) may be carried by the support ring. Alternatively, the stent(s) and the balloon(s) may be introduced later after the implantation of the support and adjustable ring either on a common assembly or on separate assemblies. The inflatable balloon(s) may be arranged inside the stent(s) and expands due to the introduction of a fluid, for example gas, or a liquid or gel.

(G) Additionally or alternatively, the (at least one) deployable pressing element may comprise a radially expandable structure such as a cage-like structure or a parallelogram structure, i.e., a "crick" or a pantograph.

The crick comprises a basis attached to the support ring. Two ratchets extend basically perpendicular to the basis. The ratchets can move in two counterratchets by applying a force. Preferably, the force is applied with an actuator. On top of the ratchets near the adjustable ring, vis a vis the basis, a further plate is arranged. This further plate is moved inwardly by moving the ratchets in the counterratchets.

The crick or the cage may be radially expandable by a pulling force or through a fluid under pressure. The crick or the cage may be carried by the support ring. The pantograph comprises two side portions and bars which are mechanical linkage connected in a manner based on parallelograms, extending between the side portions. A plate is arranged on top of the bars near the adjustable ring. The plate is extending inwardly when at least one side portion is moved towards the other side portion. The parallelograms change their shape during the process but remain parallelograms. Preferably both side portions are moved towards each other. During this moving process, crossing points of the bars basically remain at their positions. The other corners preferably attached to the side portions of the parallelograms move inwardly during the moving process.

Alternatively, the pantograph does not comprise side portions but only mechanical linkage connected bars in a manner based on parallelograms and the plate on top of it. By moving the outer corners of the bars towards each other, the plate is moved inwardly.

(H) Additionally or alternatively, the (at least one) deployable pressing element may comprise a rotatable cam like structure.

The cam like structure may be embedded into the support ring. The cam like structure can be rotated about an external pivot point. The external pivot point may be embedded into the support ring. By rotation of the cam like structure about the external pivot point one end of the cam like structure pushes the adjustable ring inwardly. The deployment is dependent on the rotated angle.

A further independent aspect of the invention (optionally usable in combination with any of the aforementioned features) may provide an adjustable annuloplasty ring assembly comprising at least one adjuster for adjusting a shape of the ring assembly, the adjuster comprising a fluid-deployable device (for example, comprising an inflatable bladder; and/or a movable diaphragm; and/or a piston within a cylinder).

A further independent aspect of the invention (optionally usable in combination with any of the aforementioned features) may provide an annuloplasty ring (e.g., and adjustable annuloplasty ring) with at least one sensor for sending a parameter relating to performance of a valve to be treated by the annuloplasty ring. Optionally, the sensor may comprise at least one selected from: a Doppler-effect sensor for sensing blood flow; a transducer for a Doppler-effect sensor; a current transducer to work the other sensors based on the blood flow; an acoustic transducer; an ultrasound transducer; a pressure sensor for sensing blood pressure; a pH electrolyte sensor etc.

A further independent aspect of the invention (optionally usable in combination with any of the aforementioned features) may provide an annuloplasty ring (e.g., and adjustable annuloplasty ring) with at least one electrode for applying or sensing an electrical signal at the site of the cardiac valve, in particular a defibrillation electrode.

A further aspect of the invention (optionally usable in combination with any of the aforementioned features) may provide a system including: an adjustable annuloplasty ring or ring assembly, optionally as defined above; an actuator for generating physical adjustment controls for transmission to the ring; and a transmission line for coupling the actuator to the ring for transmitting the physical adjustment controls from the actuator to the ring.

The system may include one or more of the following features, which are all optional:

(A) The transmission line may be made at least partly (and optionally substantially entirely) of material that is biodegradable and/or resorbable in the human body.

(B) The transmission line may further serve as a cable for a communication with the sensor to e.g. apply an electric shock for cardioversion.

(C) A releasable coupling may be provided for releasably coupling the transmission line to the ring or ring assembly.

(D) The annuloplasty ring may have plural adjusters (e.g. pressing elements) for adjusting a shape of the ring, and the actuator may be configured for controlling the plural adjusters.

For example, the system may be configured for controlling actuation in at least one predetermined sequence.

Also for example, the system may be configured for compulsory actuation of at least one adjuster associated with a lateral portion of the ring, before actuation of an adjuster associated with a posterior and/or anterior portion.

Also for example, (and optionally as a result of compulsory lateral adjustment first, as above), the system may be configured to control an order of actuation of the adjusters in such a manner as to provide reinforcement of a mitral valve without provoking onset of substantial systolic anterior motion (SAM) of the anterior mitral valve leaflet. An anterior leaflet may be turned away from ventricle's lateral wall. Therewith, the risk of occlusion of a left ventricle outflow tract after annulus activation is reduced.

Also for example, (and optionally as a result of lateral adjustment first, as above), the annuloplasty ring and therefore the annuloplasty region have a more anatomic shape.

(E) The transmission line (optionally for transmission of mechanical force) may comprise at least one helical or non-helical coil and having plural coil turns. The coil turns may be configured to permit axial flexibility of the transmission line in the absence of axial compression force, and the coil turns bearing axially against one another in response to axial compression force to provide column strength for transmitting the axial compression force along the transmission line.

The transmission line may be constructed as a catheter comprising a lumen.

The above aspects may be used independently, but also advantageously in combination. The preferred embodiment illustrates all aspects in combination.

A further independent aspect provides an adjustable annuloplasty ring assembly comprising a support ring, an adjustable ring nested at least partly within the support ring, and at least one deployable pressing element for deforming the adjustable ring using the support ring as support. Plural pressing elements may be used at different positions around rings. Each pressing element may have a variable extents of deployment, to vary the extent of deformation of the adjustable ring at the position of the pressing element. Each pressing element may comprise a deflectable blade, and the state of the blade may be retained by a ratchet. The pressing elements may be operated in a predetermined controlled sequence.

While certain aspects, features and ideas have been set out above and in the appended claims, protection is claimed for any novel idea or feature combination described herein and/or illustrated in the drawings, whether or not emphasis has been placed thereon.

BRIEF DESCRIPTION OF THE DRAWINGS

Non-limiting embodiments of the invention are described, by way of example only, with respect to the accompanying drawings, in which:

FIG. 4 is a flow diagram illustrating actuator control steps;

FIG. 5a, b are flow diagrams illustrating adjustment steps;

DETAILED DESCRIPTION OF PREFERRED EMBODIMENTS

Figure 1:
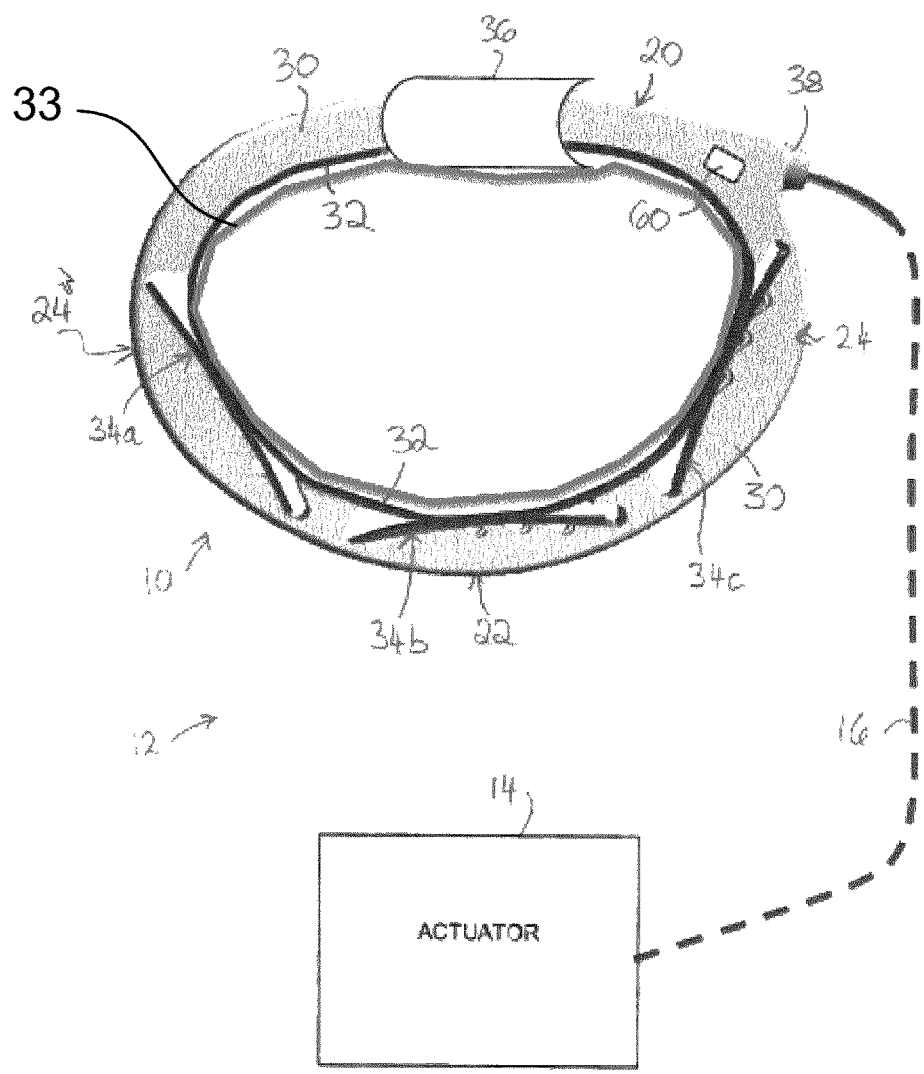
FIG. 1 is a schematic view of an annuloplasty ring system, including an annuloplasty ring assembly and an actuator.
Figure 2:
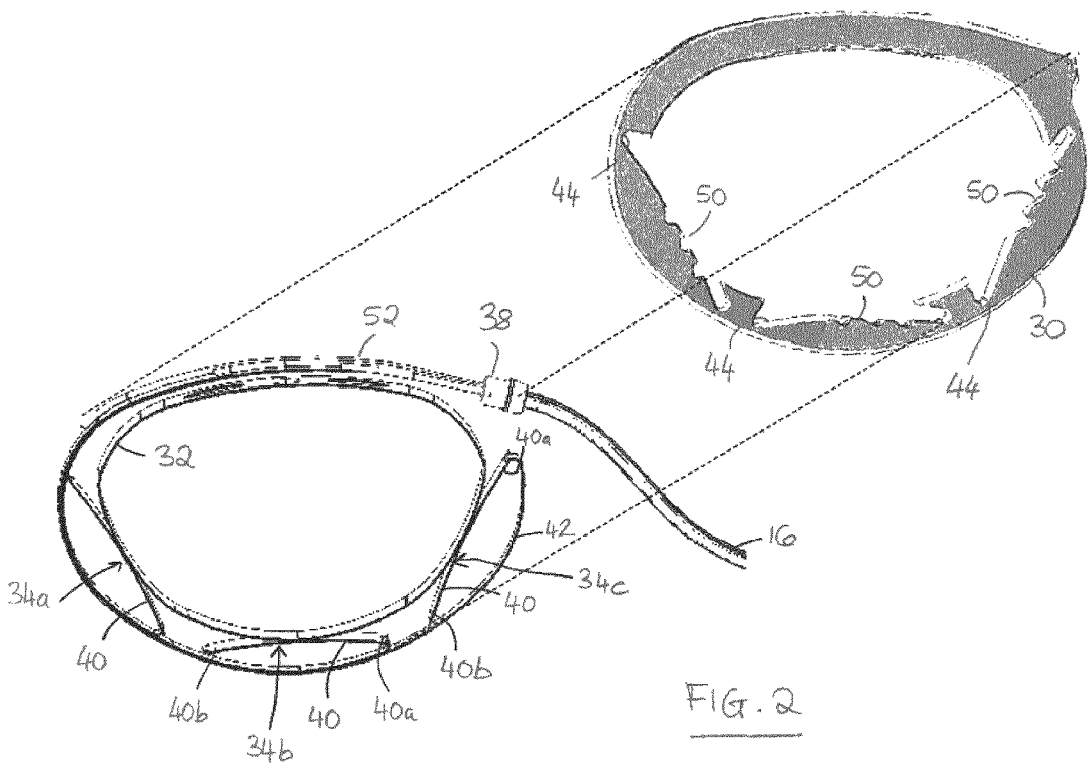
FIG. 2 is a schematic exploded view of the assembly of FIG. 1.
Figure 3:
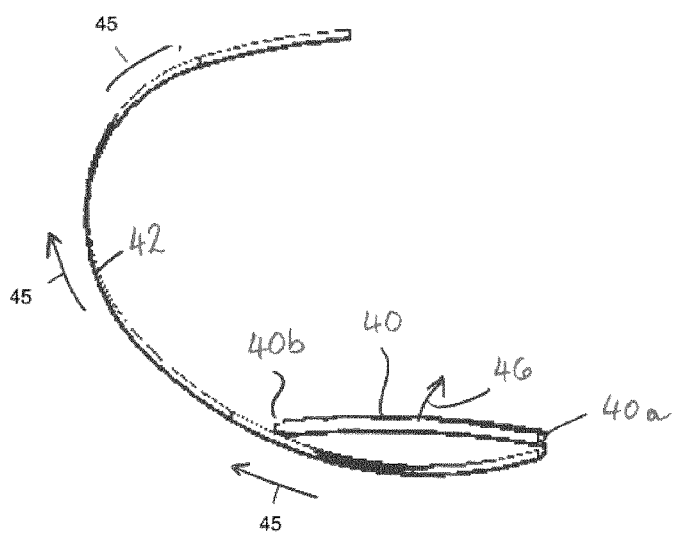
FIG. 3 is a schematic view of a single pressing element in isolation, and illustrating how the pressing element is deployed in response to mechanical force applied by a control member.

Referring to FIGS. 1-3, an annuloplasty ring assembly 10 is illustrated. The ring assembly 10 may optionally be part of a system 12 that further includes an actuator 14 coupled (or couplable) to the ring assembly 10 by one or more transmission lines 16. The ring assembly 10 may be adjustable, for example after implantation in the human body, by means of the actuator 14 and transmission line 16.

The ring assembly 10 may be configured for annuloplasty of a human cardiac valve, for example, an atrioventricular valve, such as a mitral valve or tricuspid valve. The configuration of the ring assembly 10 may be chosen depending on which cardiac valve the assembly 10 is intended to treat. The term "ring" (including "ring" assembly) as used herein is intended to cover any shape for circumscribing at least a majority of a periphery of a valve annulus. A ring may be closed (e.g., generally "O" shaped or generally "D" shaped) or a ring may be open (e.g., generally "C" shaped). A ring may be generally round or of generally circular geometry (e.g., generally "O" shaped or generally round-"C" shaped). Such a shape may optionally be selected for a tricuspid valve ring. Alternatively, a ring may be non-round (e.g., generally "D" shaped or generally elongate-"C" shaped). Such a shape may optionally be selected for a mitral valve ring. A ring may optionally be split and/or may optionally extend around more than 360 degrees in some cases. Such a ring may provide some characteristics of a closed ring (e.g., enclosing an area completely), with other characteristics of an open ring (e.g., movable end portions may accommodate more easily a larger range of size variation than a permanently closed ring).

The ring may be bent, generally saddle-shaped. The saddle may generally be in the form of a bent an "O", "C", or "D".

The illustrated ring assembly 10 has a generally "D" shape suitable for implantation around the mitral valve of the human heart. However, it is emphasized that the same principles may be used in other embodiments having different ring shapes or configurations. The "D" shape may comprise a generally straight (or least curved) anterior portion 20 for fitting near the anterior valve leaflet, a generally curved (or more curved) posterior portion 22 opposite the anterior portion 20 and for fitting near the posterior valve leaflet, and two lateral portions 24.

In some embodiments, the ring assembly 10 generally comprises an (e.g., outer) support ring 30, an (e.g., inner) adjustable ring 32 nested at least partly within the support ring 30, and at least one adjuster for adjusting a shape of the ring assembly. The adjuster may be or comprise a pressing element, for example, in the form of a deployable pressing element 34, for deforming the adjustable ring 32 by using the support ring 30 as a support, for adjusting the shape of the adjustable ring 32. (In the present description, the reference 34 may be used to refer to one or more pressing elements in general; the pressing elements are labeled in the drawings as 34a-c).

In some embodiments, the support ring 30 may be more rigid in shape than the adjustable ring 32 to act as a shape support for the assembly. The adjustable ring 32 may be deformable to permit the adjustable ring 32 to adopt a shape under the effect of the at least one pressing element 34. The shape and size of the adjustable ring 32 may determine (or at least influence) the positioning and extent of the corrective bracing effect of the ring assembly on and/or around the native valve annulus to be treated.

The adjustable ring 32 may be sutured to a valve annulus, e.g. the mitral valve annulus. Alternatively, the adjustable ring 32 is connected to the valve annulus with other surgical means used for valve repair/replacement such e.g. hooks, barbs or the like. There may also be a cover around the support ring 30 and the adjustable ring 32. The cover has a suture area 33 to suture the assembly to the valve annulus. Alternatively, there is no cover around the support ring 30. The suture area to suture the assembly to the valve annulus is constructed as an inner line or area on the support ring 30.

Suitable material or materials for the support ring 30 and the adjustable ring 32 include, for example, metal (for example, stainless steel, and/or titanium, and/or steel-chrome-cobalt alloy) and/or biocompatible medical grade plastics (for example, PET or PEEK). The rings 30 and 32 may be made of the same material as each other, or of different materials from each other. In some embodiments, the support ring 30 may be of titanium, and the adjustable ring 32 made of steel-cobalt-chrome alloy.

In the illustrated example, both the support ring 30 and the adjustable ring 32 have a closed ring configuration. However, one or both of the rings 30 and 32 may optionally have an open or split ring configuration if desired. In particular, it is envisaged that the adjustable ring 32 may have a split ring configuration comprising end portions that are able to slide past each other or one end slide into the other end, for accommodating a range of different sizes while retaining a near-closed peripheral shape.

The ring assembly 10 may further comprise a flexible cover 36 covering at least partly, at least one of the rings 30 and 32 (and optionally covering the rings 30 and 32 substantially entirely except for a port 38 for the transmission line 16). In FIG. 1, only a portion of the cover 36 is illustrated to avoid obscuring the other structure of the assembly 10. However, it will be appreciated that the cover 36 may extend substantially entirely around the combined extent or footprint of both rings 30 and 32. Specific design examples for the cover 36 are discussed later.

In the illustrated embodiment, the at least one pressing element 34 may be carried by or in the support ring 30, and may press against the adjustable ring 32 when deployed. In some alternative embodiments, the pressing element 34 may be carried instead by the adjustable ring 32.

In some embodiments, the ring assembly 10 comprises plural deployable pressing elements 34a-c provided at different positions around an interface between the support ring 30 and the adjustable ring 32. Each pressing element 34a-c may be deployable to deform the adjustable ring 32 inwardly with respect to the support ring 30 at the respective position of each pressing element 34a-c. In the present example, three pressing elements 34a-c are provided. The pressing elements 34a-c may optionally be organized as lateral pressing elements 34a and 34c associated (at least partly) with the lateral portions 24 of the ring assembly 10, and a posterior pressing element 34b associated with the posterior portion 22. Other positions and numbers of pressing elements 34 around the interface between the support ring 30 and adjustable ring 32 are also envisaged.

In some embodiments, the (at least one) pressing element 34 may be controllable to have a variable extent of deployment at the position of the pressing element 34, to define a variable deformation of the adjustable ring 32 with respect to the support ring 30. The assembly may be configured for retaining a state of deployment of the pressing element 34 after adjustment. The assembly may be configured for defining a plurality of predetermined different deployment states representing different extents of deployment, at each of which the deployment state is retainable. In some embodiments, the plurality of predetermined different states may correspond to retaining positions defined by a ratchet.

Various implementations of pressing element 34 are envisaged. In the illustrated example, each pressing element 34 comprises a blade 40 (as illustrated in FIGS. 2 and 3). The blade 40 may be configured to deflect or bow in response to mechanical force applied to a portion of the blade. For example, the blade 40 may be carried by the support ring 30 and configured to deflect or bow inwardly towards the adjustable ring 32 in response to the mechanical force. The mechanical force may be applied for example, to at least one end of the blade 40. In the illustrated form, a control member 42 extends from one end 40a of the blade for application of force. An opposite (e.g., free) end 40b of the blade 40 is restrained by a stop profile 44 of the support ring 30 against which the end 40b bears. Referring to FIG. 3, application of tension (as indicated by arrow 45) through the control member 42 draws the end 40a towards the end 40b, causing the blade 40 to bow to a deployed state, as indicated by arrow 46. The extent of deployment is controllable by the amount of displacement applied via the control member 42. Greater displacement increases the extent of bowing, and the extent to which the blade deploys or projects.

As can be seen in FIGS. 2 and 3, the blade 40 may have a shape when in its non-deployed state, that promotes bending or bowing of the blade consistently in a predetermined deployment direction, for example, towards the adjustable ring 32 (and not, for example, in an opposite direction away from the adjustable ring 32). The blade 40 may have a non-straight shape, for example, just partially or slightly bowed in the desired direction. With such a configuration, the direction of bowing is preset in the blade, such that application of mechanical force will consistently bow the blade 40 towards the adjustable ring 32. The non-deployed shape may be a natural shape of the blade 40, or it may be a shape imparted to the blade, for example, by a profile shape of the portion of the support ring 30 supporting the blade 40.

A latching (e.g., self-latching) mechanism may be provided, for example, in the form of a ratchet 50, for retaining the pressing element 34 (e.g., blade 40) in a state of deployment to which the pressing element has been moved. In the present example, the latch (e.g., ratchet 50) may define the plurality of predetermined different deployment states referred to earlier. The ratchet 50 may be configured to allow the blade 40 to be progressively or incrementally moved to increase the extent of deployment, by application of force via the control member 42. The ratchet 50 may be configured to obstruct relaxing of the blade 40 back towards the non-deployed condition (at least until an optional reset control is activated, described later).

By providing a latching mechanism (e.g. ratchet 50) for retaining the deployment state of the pressing element 34 (e.g., blade 40), the shape of the adjustable ring 32 can be set and preserved even if the actuator 14 and/or the control line 16 is/are subsequently disconnected from the ring assembly 10. It can also avoid needing to maintain mechanical tension in the control line 16 to preserve the deployment state of each pressing element 34.

Various implementations of ratchet 50 are envisaged. In the illustrated example, the ratchet 50 cooperates directly with the blade 40, for example, with the end 40a of the blade 40. The ratchet 50 may be provided by a sawtooth profile of an edge or surface of the support ring 30 against which the end 40a bears. The number of ratchet positions may be chosen as desired. In the illustrated form, the ratchet has four ratchet positions (corresponding to a non-deployed state, and three valleys of the sawtooth profile in which the end 40a of the blade 40 can locate progressively in a first party deployed state, a second further deployed state, and a third fully deployed state). However, a greater number of positions (e.g. four, five, six or more), or a smaller number of positions (e.g. one, two or three), could be implemented as desired. In the illustrated form, each of the pressing elements 34 has the same number of ratchet positions (e.g. three (or four including the non-deployed position)), but different pressing elements 34 could be provided with a respective different number of ratchet positions if desired.

In an alternative form (not shown), a latching mechanism (e.g. a ratchet) could be implemented elsewhere in or on the support ring 30, for example, acting on the control members 42 near the port 38. However, the illustrated form may provide good and reliable functionality, in a compact design, with few moving parts.

In some embodiments, the ratchet 50 includes an override feature allowing the ratchet effect to be overridden, such that the blade 40 may relax from a retained deployment state back towards, or to, the non-deployed state. The override feature may be operated in response to an additional control member (not shown), and/or in response to mechanical force applied to a combination of the control members 42 in unison. The override feature may be operable for each latch 50 individually and/or independently of the others, or the override feature may be operable for all latches 50 in unison for relaxing all of the blades 40 in unison.

The control members 42 extending from the respective different blades 40 may extend in a generally circumferential or peripheral direction within the support ring 30, towards the port 38. In the illustrated form, each control member 42 is an integral extension of the respective blade 40, that is folded at the end 40a of the blade 40. In other forms, the control members 42 could be separate members coupled to the blades. Any suitable material may be used for the blades 40 and/or the control members 42. Suitable material or materials include, for example, metal (for example, stainless steel, and/or titanium, and/or steel-chrome-cobalt alloy) and/or biocompatible medical grade plastics (for example, PET or PEEK). In some embodiments, the integral blades 40 and control members 42 are of steel-cobalt-chrome alloy.

The blades 40 may optionally be capable of bowing elastically.

The control members 42 extend to a coupling 52 for coupling each control member 42 to a respective tension filament of the transmission line 16. The coupling 52 may optionally be releasable for enabling the transmission line 16 to be disconnected. The coupling 52 may optionally allow reconnection of the transmission line 16 after a disconnection.

In other embodiments (not shown), the (at least one) adjuster or pressing element 34 may comprise a fluid-deployable device. The fluid-deployable device may, for example, comprise an inflatable bladder; and/or a movable diaphragm; and/or a piston within a cylinder. The operating fluid may, for example, be a gas (e.g., for pneumatic control), or a liquid or gel (e.g., for hydraulic control) or electro-active polymers (e.g., for electronic control).

In one form, a hardenable fluid may be introducible. The extent of deployment of the fluid-deployable device may remain adjustable while the inflation fluid remains fluid. The deployment state may become set when the fluid hardens. By hardening the fluid, any risks of accidental or natural leakage of fluid may be avoided.

In one form, a non-hardenable fluid may first be introduced and retained during a period while further adjustment of the annuloplasty ring may be desired. Upon reaching a treatment stage such that no further adjustment is desired, the non-hardenable fluid may be replaced by (or augmented by) a hardenable fluid (or component), to set the final deployment state.

In another embodiment (not shown), the (at least one) adjuster or pressing element 34 may comprise an expandable stent. The expandable stent may comprise an inflatable balloon or balloon in order to expand. The inflatable balloon may be inflated with a fluid such as gas, liquid or gel.

Referring to FIG. 1, and as described above, the flexible cover 36 may cover at least partly, at least one of the rings 30 and 32 (and optionally covering the rings 30 and 32 substantially entirely except for the port 38 for the transmission line 16). The flexible cover 36 may serve as an atraumatic contact surface against the heart tissue, and/or as a suturable surface for suturing to the heart tissue, and/or as an emboli protection filter for trapping any blood clots.

The flexible cover may be configured to accommodate the extent of shape variation of the adjustable ring 32 with respect to the support ring 30. In some embodiments, the extent of shape variation and/or the shape accommodation of the cover may correspond to variation of an inner dimension of the adjustable ring 32 (e.g. inner radius, or inner diameter, or inner peripheral length) of at least 2 mm, or at least 3 mm, or at least 30% of a maximum value of the dimension. In some embodiments, the flexible cover 36 may be of stretchable material (e.g. elastically stretchable material) able to conform to the shape variation of the adjustable ring 32. Alternatively, the cover 36 may be of substantially non-stretching material and be "oversized" in order to accommodate shape variation of the adjustable ring 32. Any suitable material may be used for the cover 36. The material may be fabric, e.g., polyester fabric.

The ring assembly 10 may optionally further comprise one or more sensors and/or electrodes, indicated generally at 60. The sensor and/or electrode 60 may be supported by the support ring 30, and optionally carried by the cover 36 or by the support ring 30. A sensor 60 may be configured for sensing a parameter relating to performance of a valve to be treated. For example, a sensor may be a Doppler-effect sensor or a transducer therefore (e.g. an acoustic transducer, such as an ultrasound transducer) for sensing blood flow; or a pressure sensor for sensing blood pressure; or a cardiac rhythm sensor to detect atrial arrhythmias (e.g. flutter or atrial fibrillation). Additionally or alternatively, the sensor 60 may sense regurgitation with the aid of acoustic or ultrasonic sensors. The sensing of regurgitation is an indication of the correction performance and the effects of the adjustment could directly be recognised by the sensor 60 and transmitted to an operator. An electrode 60 may be an electrode for applying or sensing an electrical signal at the site of the cardiac valve to be treated. More than one sensor/electrode 60 may be provided if desired, and the position(s) on the assembly 10 may be varied as desired to suit a specific design configuration of the assembly 10.

Referring to FIG. 1, the transmission line 16 may serve to couple the annuloplasty ring assembly 10 to an actuator 14. At the same time, transmission line 16 may also serve as a cable for communication with the sensor 60. The actuator 14 may, for example, be a subcutaneous actuator controllable percutaneously or wirelessly, or the actuator 14 may be external to the patient's body. For the type of mechanically operated or adjusted pressing elements 34 illustrated in FIGS. 1 to 3, the actuator 14 may generate controllable tension and/or controllable displacement of a respective filament for transmission to the control member 42 for actuating a respective pressing element 34 (e.g., blade 40). Various designs and types of actuator 14 are envisaged. For example, the actuator 14 may be electronic or electrically operated, or fluid operated, or mechanical.

In some embodiments, the transmission line 16 from the actuator 14 to the ring assembly 10 may be flexible. The transmission line 16 may be configured to provide sufficient column strength to transmit the reaction force to the applied actuation tension. The transmission line 16 may be a single conduit for multiple filaments, or the transmission line 16 may include multiple conduits, for example, one for each filament. The transmission line 16 may, for example, comprise a coiled and/or spiral conduit. The conduit 16 may comprise at least one helical or non-helical coil. The conduit 16 may have plural coil turns. In the absence of tension applied by the actuator, there is no reaction force in the conduit, and the coils may be relatively loose to provide high flexibility. When tension is applied by the actuator 14 to a filament within the conduit, the coils or turns of the conduit may collapse or compress in an axial direction, to bear axially against one another, and provide column strength for the reaction force to the applied tension. The column strength within the conduit of the transmission line 16 can provide a reference between, for example, the support ring 30 and a housing of the actuator 14, to enable application of tension via a filament within the transmission line 16.

In some embodiments the transmission line 16 might be a hollow tube (i.e., a catheter) through which an inflatable balloon may be inserted to deploy the adjustable ring.

The transmission line 16 may be detachable from the ring assembly 10. The actuator 14 and/or the transmission line 16 may be easily retrieved after detachment.

The filament and the conduit of the transmission line 16 may be made of any suitable material. Suitable material or materials include, for example, metal (for example, stainless steel, and/or titanium, and/or steel-chrome-cobalt alloy) and/or biocompatible medical grade plastics (for example, PET or PEEK). The filament and the conduit may be made of the same material as each other, or of different materials from each other. In some embodiments, the filament and the conduit are both made of steel-cobalt-chrome alloy.

In alternative embodiments, the transmission line 16 may be made of materials that are substantially entirely resorbable by the body. A suitable resorbable material may, for example, be polyglactin. This can permit the annuloplasty ring assembly 10 to become autonomous and may in some cases be advantageous in avoiding a later surgical or percutaneous procedure if desired to remove a permanent transmission line 16 extending to the heart.

In some alternative embodiments (not shown) in which fluid-deployable adjusters or pressing members 34 are used, transmission line 16 may comprise at least one fluid conduit, and the actuator 14 may control fluid supply to, and/or from the ring assembly 10 to perform desired adjustment. The actuator 14 may also control introduction of a hardenable fluid, or hardenable (or hardening) fluid component, as already described.

FIGS. 4 and 5 illustrate schematically example flow diagrams of processes for controlling adjustment of the annuloplasty ring assembly 10. In FIG. 4, after implantation at a cardiac valve (step 70), a first adjustment procedure 72 may be performed for adjusting the ring assembly 10 to impart a preliminary correction to the cardiac valve. Subsequently, at a later time (for example, weeks, months or even years later), a second adjustment procedure 74 may be performed for increasing the corrective effect of the ring assembly 10. Additional subsequent adjustment procedures (not shown) may also be used.

By performing the adjustment in progressive procedures following implantation, the corrective effect of the annuloplasty ring assembly 10 can be applied progressively, in gentle or modest increments. This may enable the person's heart to adapt more easily to each adjustment. In particular, it can avoid a dangerous situation in which a patient's heart may become too stressed by an abrupt large correction to the valve anatomy. A large adjustment may be too great a shock for the heart, especially a heart already affected by incompetent valve function. The invention can avoid unnecessary risk to the patient's wellbeing.

Referring to FIG. 5, whether or not different adjustment may be carried out in different procedures, the system 12 may be configured for controlling adjustment of the shape of the adjustable ring 32 in a predetermined sequence. For example, the sequence may involve adjustment of at least one lateral pressing element 34a or 34c, before adjustment of a posterior/anterior pressing element (here posterior pressing element 34b). In FIG. 5a, the sequence is: adjustment of a first lateral pressing element 34a/c (step 80); adjustment of a second lateral pressing element 34a/c (step 82); adjustment of the posterior pressing element 34b (step 84). Alternatively, in FIG. 5b, the order of steps 82 and 84 is reversed.

It is believed that, most especially in the case of mitral valve treatment, by using a sequence in which at least one lateral adjustment is made prior to an anterior/posterior adjustment, the valve can be reinforced and/or deformed to correct valve function with less risk of provoking onset of substantial systolic anterior motion (SAM) of the anterior mitral valve leaflet. Such a sequence can therefore provide an extremely advantageous contribution to the treatment of mitral valves, while mitigating the risk of SAM.

The predetermined sequence may be implemented by an electronic control, or by a mechanical lock-out (for example, in the actuator 14 or the ring assembly 10) that prevents the posterior pressing element 34b from being adjusted until one (or both) lateral pressing elements 34a and 34c have first been adjusted.

The sequence of adjustment may also be controlled such that each pressing element 34 may only be adjusted by a single increment in the deployment state. This may prevent, for example, one of the pressing elements 34 from being adjusted to an extreme deployed state before adjacent pressing elements have been adjusted to near states. By limiting to only incremental adjustment, a failsafe may be provided against application of highly distorted corrections that deviate significantly from the native valve annulus shape.

As explained previously, the ratchet 50 of each pressing element 34 may include an override feature to all the pressing elements 34 to be relaxed to or towards their non-deployed states, for example, under control from the actuator 14. The override feature may allow the ring assembly 10 to be "reset" if, for example, too extreme deformation has been applied by an adjustment, or if the relaxing of the annuloplasty ring becomes appropriate due to morphology of the patient's heart or native valve annulus.

It is emphasized that the foregoing description is merely illustrative of a preferred non-limiting form of the invention. Many modifications, improvements and equivalents may be used within the scope and/or principles of the invention.

Figure 6:
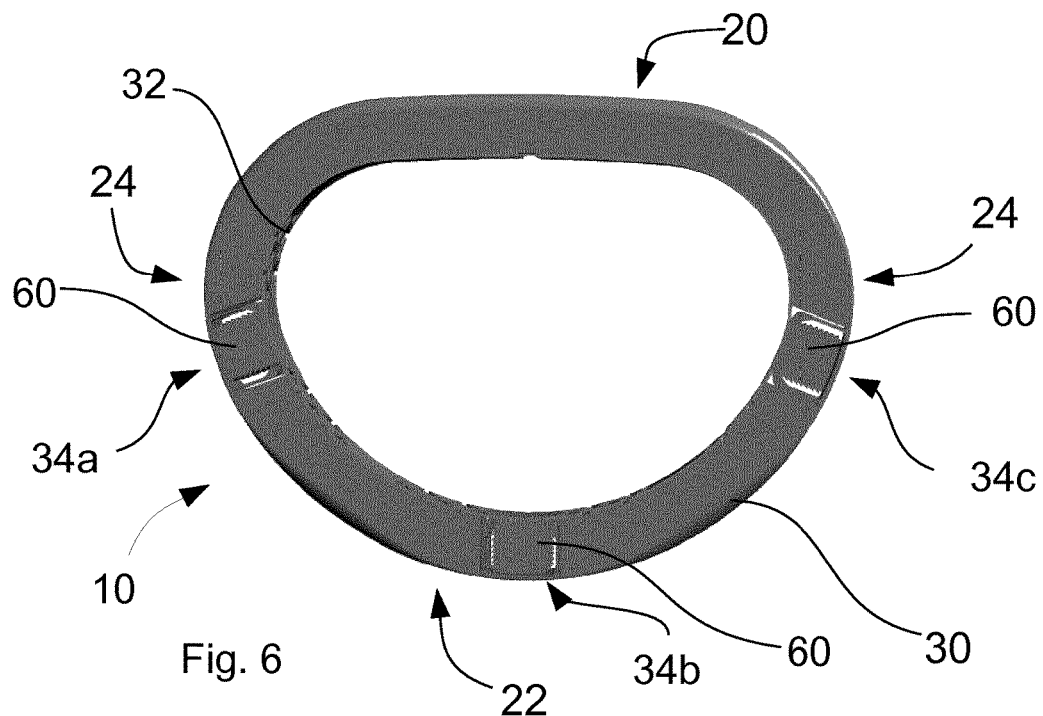
FIG. 6 is a schematic view of an annuloplasty ring system, including cricks.
Figure 7:
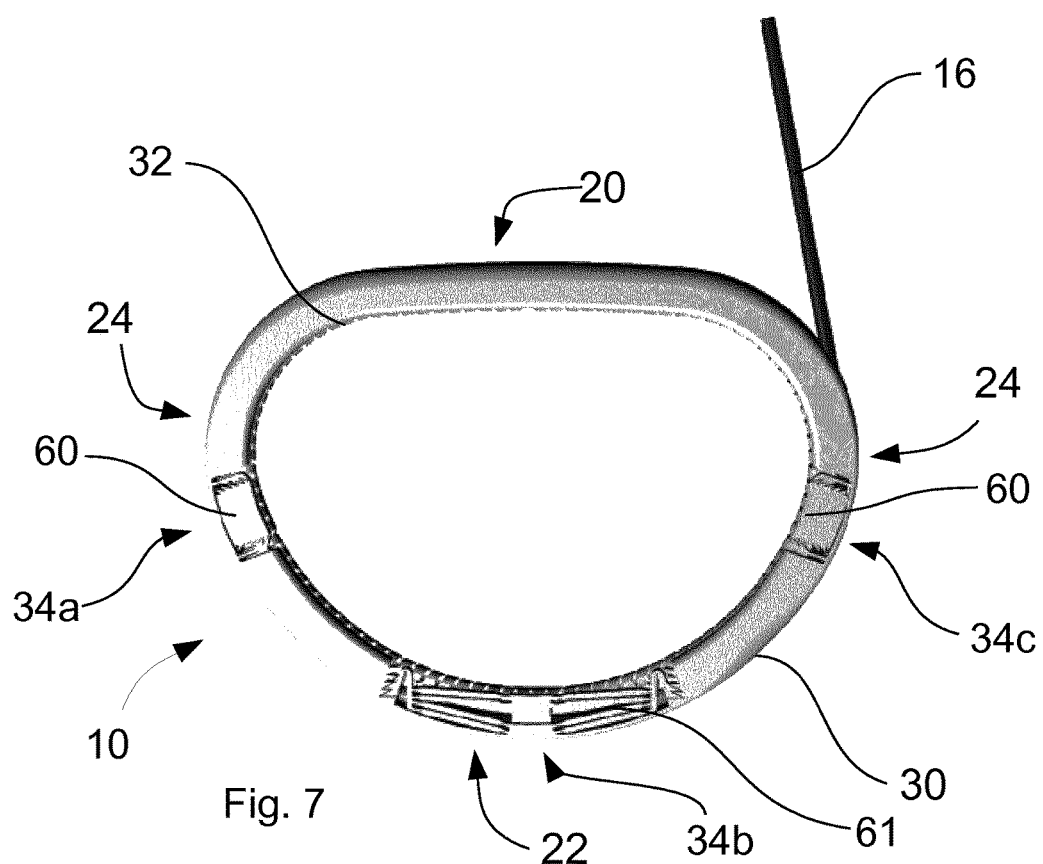
FIG. 7 is a schematic view of an annuloplasty ring system, including cricks and a pantograph.

Referring to FIG. 6, three pressing elements 34 comprising a crick 60 are shown. The cricks 60 are attached to the support ring 30 with one end. The cricks 60 may be actuated by an actuator 14 (not shown). Each crick 60 comprises two ratchets and counterratchets. The crick 60 may be pushed towards the adjustable ring 32 by moving the ratchets in the counterratchets. Each crick 60 can be moved by several millimeters towards the adjustable ring 32. Preferably, the lateral pressing elements 34a, c are moved firstly, and the posterior pressing element 34b is moved after the two lateral pressing elements 34a, c have been adjusted. The cricks 60 allow a smooth and controlled adjustment of the adjustable ring 32 to the preferred position. In FIG. 7, the posterior pressing element 34b comprises a pantograph 61 instead of a crick 50. The lateral pressing elements 34a, c comprise a crick 60 as in FIG. 6. The pantograph may additionally or alternatively be arranged at one or both lateral portions 24. The pantograph 61 can be moved further than the cricks 60, allowing for a bigger reduction of the anterior-posterior diameter than with a crick 60. The pantograph 61 comprises two lateral portions. One of lateral portions may be fixed and the other one moveable in the direction of the first one, thereby extending two wires which form multiple parallelograms in the direction of the adjustable ring 32. Therewith, the adjustable ring 32 the posterior-anterior diameter is reduced. Alternatively, both lateral portions of the pantograph are movable to extend the wires in the direction of the adjustable ring.

The invention claimed is:

1. An adjustable annuloplasty ring assembly comprising:
   a support ring,
   an adjustable ring nested at least partly within the support ring, and
   a plurality of pressing elements at different positions around an interface between the support ring and the adjustable ring, each pressing element deployable to deform the adjustable ring inwardly using the support ring as a support, for adjusting the shape of the adjustable ring the at least one deployable pressing element comprises a fluid-deployable device.

2. The assembly of claim 1, wherein each pressing element is deployable to deform the adjustable ring inwardly with respect to the support ring at the respective position of the pressing element.

3. The assembly of claim 1, wherein each pressing element is deployable individually.

4. The assembly of claim 1, wherein there are three deployable pressing elements.

5. The assembly of claim 1, wherein the assembly comprises an anterior portion for fitting near an anterior native cardiac valve leaflet, a posterior portion opposite the anterior portion and for fitting near a posterior native cardiac valve leaflet, and at least one lateral portion between the posterior and the anterior portions;
the plurality of deployable pressing elements comprise at least one pressing element associated at least partly with the lateral portion, and at least one pressing element associated with the posterior and/or the anterior portions.

6. An adjustable annuloplasty ring assembly, the assembly comprising:
a support ring,
an adjustable ring nested at least partly within the support ring, and
at least one pressing element deployable to deform the adjustable ring by using the support ring as a support, for adjusting the shape of the adjustable ring,
wherein at least a portion of the at least one deployable pressing element is configured to remain, in use during deployment of the pressing element, generally at a predetermined position along a periphery of at least one of the rings.

7. The assembly of claim 6, wherein the at least one deployable pressing element is configured to remain, in use during deployment of the pressing element, generally at a predetermined position along a periphery of at least the support ring.

8. An adjustable annuloplasty ring assembly, the assembly comprising:
a support ring,
an adjustable ring nested at least partly within the support ring, and
at least one pressing element deployable to deform the adjustable ring by using the support ring as a support, for adjusting the shape of the adjustable ring,
wherein the at least one pressing element is controllable to have a variable extent of deployment at the position of the pressing element, to define a variable deformation of the adjustable ring with respect to the support ring.

9. The assembly of claim 8, further comprising a control member for controlling the extent of deployment of the pressing element.

10. The assembly of claim 8, comprising a latching mechanism for retaining a state of deployment of the pressing element after adjustment.

11. The assembly of claim 1, wherein the at least one pressing element is carded by the support ring.

12. An adjustable annuloplasty ring assembly, the assembly comprising:
a support ring,
an adjustable ring nested at least partly within the support ring, and
at least one pressing element deployable to deform the adjustable ring by using the support ring as a support, for adjusting the shape of the adjustable ring,
wherein the at least one deployable pressing element comprises a fluid-deployable device.

13. The assembly of claim 12, wherein the fluid-deployable device is selected from:
an inflatable bladder;
a movable diaphragm; and
a piston within a cylinder.

14. The assembly of claim 12 wherein the fluid-deployable device is deployable by fluid selected from: a gas; a liquid; a gel.

15. The assembly of claim 1, further comprising a flexible cover for covering at least partly at least one of the rings.

16. A system comprising:
an adjustable annuloplasty ring assembly;
an actuator for generating a physical control signal for transmission to the ring assembly;
a transmission line for coupling the actuator to the ring assembly for transmitting the physical control signal from the actuator to the ring assembly; and
a releasable coupling for releasably coupling the transmission line to the ring assembly.

17. The system of claim 16, wherein the physical control signal is selected from:
a mechanical adjustment force;
a fluid control;
a pneumatic control; or
a hydraulic control.

18. A system comprising:
an adjustable annuloplasty ring assembly having a plurality of actuatable adjusters for adjusting a shape of at least a portion of the ring assembly after implantation in the body; and
an actuator for controlling actuation of the plurality of adjusters,
wherein the ring assembly comprised an anterior portion for fitting near an anterior valve leaflet of a cardiac valve to be treated, a posterior portion opposite the anterior portion and for fitting near a posterior valve leaflet, and at least one lateral portion between the posterior and anterior portions; and
wherein the system is configured for actuation of at least one adjuster associated with the lateral portion, before actuation of an adjuster associated with the posterior and/or anterior portion.

19. The system of claim 18, wherein the system is configured to actuate the plurality of adjusters in at least one predetermined sequence of actuation.

20. The system of claim 18, wherein the system is configured to control an order of actuation of the adjusters in such a manner as to provide reinforcement of a mitral valve without provoking onset of substantial systolic anterior motion (SAM) of the anterior mitral valve leaflet.

21. A system comprising:
an adjustable annuloplasty ring assembly having at least one fluid-deployable device for adjusting a shape of at least a portion of the ring assembly after implantation in the body; and
a controllable actuator for controlling flow of fluid to and/or from the fluid-deployable device.

22. The system of claim 21, wherein the fluid-deployable device is selected from:
an inflatable bladder;
a movable diaphragm; or
a piston within a cylinder.

23. The system of claim 21, wherein the fluid is selected from:
 a gas;
 a liquid; or
 a gel.

24. The assembly of claim 1, wherein at least a portion of the at least one deployable pressing element is configured to remain, in use during deployment of the pressing element, generally at a predetermined position along a periphery of at least one of the rings.

25. The assembly of claim 24, wherein the at least one deployable pressing element is configured to remain, in use during deployment of the pressing element, generally at a predetermined position along a periphery of at least the support ring.

26. The assembly of claim 1, wherein the at least one pressing element is controllable to have a variable extent of deployment at the position of the pressing element, to define a variable deformation of the adjustable ring with respect to the support ring.

27. The assembly of claim 26, further comprising a control member for controlling the extent of deployment of the pressing element.

28. The assembly of claim 26, comprising a latching mechanism for retaining a state of deployment of the pressing element after adjustment.

29. The assembly of claim 5, wherein the at least one pressing element is carried by the support ring.

30. The assembly of claim 6, wherein the at least one pressing element is carried by the support ring.

31. The assembly of claim 8, wherein the at least one pressing element is carried by the support ring.

32. The assembly of claim 1, wherein the fluid-deployable device is selected from:
 an inflatable bladder;
 a movable diaphragm; or
 a piston within a cylinder.

33. The assembly of claim 32, wherein the fluid-deployable device is deployable by a fluid selected from:
 a gas;
 a liquid; or
 a gel.

34. The assembly of claim 1, and comprising at least one sensor for sensing a parameter relating to performance of a valve to be treated by the assembly.

35. The assembly of claim 34, wherein the sensor comprises at least one sensor selected from:
 a Doppler-effect sensor for sensing blood flow;
 a transducer for a Doppler-effect sensor;
 an acoustic transducer;
 an ultrasound transducer; or
 a pressure sensor for sensing blood pressure.

36. The assembly of claim 1, and comprising at least one electrode for applying or sensing an electrical signal at a site of the cardiac valve.

37. The assembly of claim 34, wherein the ring assembly is adjustable, after implantation, for adjusting a shape of the annuloplasty ring assembly.

38. The assembly of claim 36, wherein the ring assembly is adjustable, after implantation, for adjusting a shape of the annuloplasty ring assembly.

39. The assembly of claim 1, wherein the assembly is adjustable, after implantation, for adjusting a shape of the annuloplasty ring assembly.

40. The assembly of claim 1, comprising a mechanical interface arranged to receive a prosthetic valve.

\* \* \* \* \*